United States Patent [19]

Sankey et al.

[11] Patent Number: 4,908,474
[45] Date of Patent: Mar. 13, 1990

[54] PREPARATION OF ESTERS

[75] Inventors: John P. Sankey, Warrington; Robert Johnson, Liverpool, both of England

[73] Assignee: Interox Chemicals Limited, London, England

[21] Appl. No.: 199,959

[22] Filed: May 26, 1988

[30] Foreign Application Priority Data

Jun. 2, 1987 [GB] United Kingdom ............... 8712909

[51] Int. Cl.$^4$ ............................................. C07C 69/76
[52] U.S. Cl. ................................................... 560/109
[58] Field of Search ......................................... 160/109

[56] References Cited

U.S. PATENT DOCUMENTS 3,925,016  12/1975  Haase ..................................... 8/169

FOREIGN PATENT DOCUMENTS

| A0105672 | 4/1984  | European Pat. Off. . |
| A0120591 | 9/1984  | European Pat. Off. . |
| A0125641 | 11/1984 | European Pat. Off. . |
| A0148148 | 7/1985  | European Pat. Off. . |
| A0153222 | 8/1985  | European Pat. Off. . |
| A0153223 | 8/1985  | European Pat. Off. . |
| A0164786 | 12/1985 | European Pat. Off. . |
| A0221045 | 5/1987  | European Pat. Off. . |
| 864798   | 4/1961  | United Kingdom . |

OTHER PUBLICATIONS

Dr. F. Püschel and Dr. O. Todorov, "Connections between the Composition and Certain Properties of Surface Active Benzene Sulphonates with Heteroatoms in the Aliphatic Side Chain, Part 3, Preparation of Sulphonates", *Tenside*, 7, 1979, Heft 5, pp. 249–254.

W. J. Hickinbottom, "Reactions of Organic Compounds", 1936, p. 98.

*Primary Examiner*—Paul J. Killos
*Attorney, Agent, or Firm*—Larson and Taylor

[57] ABSTRACT

Hitherto processes proposed in recent years for preparing esters of phenol sulphonate salts by reaction between a carboxylic acid chloride and a phenol sulphonate salt place considerable emphasis upon dehydrating the reactants before they are brought into contact in an organic solvent reaction medium.

The present invention avoids the problems of employing non-aqueous solvents by carrying out the reaction under aqueous conditions but with controlled alkalinity and water content, especially at a base to phenol sulphonate mole ratio of from 1.3:1 to 1.6:1 and a total water to phenol sulphonate (as the anhydrous material) of not more than 4.5:1. The reaction advantageously employs in preference only a small molar excess of carboxylic acid chloride over the phenol sulphonate and preferably has a reaction temperature controlled to below 30° C., expecially 5° to 20° C.

In a further improvement to the process, the difficulty of enhanced contamination with benzoic acid in the products can be ameliorated by employing a small but effective amount of a surfactant, especially an alcohol ethoxylate, in the reaction mixture.

The process is especially well suited to making sodium benzoyl oxybenzene sulphonate from sodium phenol sulphonate dihydrate and benzoyl chloride.

32 Claims, No Drawings

PREPARATION OF ESTERS

The present invention relates to the preparation of esters of oxybenzene sulphonate salts and more particularly to processes therefore in which a phenol sulphonate salt is reacted with a carboxylic acid chloride.

By way of background to the present invention, it will be recognised that within recent years there has been a trend in Europe for domestic clothes washing to operate at lower wash temperatures and in order to retain effective bleaching of stains considerable efforts have been made to incorporate bleaching agents or bleaching systems that are as active at the lower wash temperatures as conventional hydrogen peroxide/persalt bleaches have been at higher wash temperatures.

Amongst those bleaching systems that were considered during an earlier period of intense activity, namely during the late 1950's and early 1960's, that system based upon carboxylic acidoxybenzene sulphonates was the subject of considerable development. Although there was particular emphasis upon the acetoxy esters, British Patent 864798 disclosed the preparation of the n-butyrate, caproate and caprylate esters of sodium phenol sulphonate by reacting excess of the aliphatic acid anhydride with anhydrous sodium phenol sulphonate at temperatures of from 120 to 200° for several hours.

As a result of the renewed interest in use of phenol sulphonate esters, there has been a resurgence of research into methods of preparing them, and especially the $C_6$ to $C_{15}$ esters. Some continued interest has remained with the use of acid anhydrides as for example by Rhone-Poulenc Chimie de Basee in EP-A-153222 and EP-A-153223 published August 28, 1985. The reaction is carried out in a strong polar solvent, e.g. DMF so that it is necessary to add an anti-solvent, acetone, to the reaction mixture to remove the ester from solution and to separate the acetone and DMF before the solvent can be reused. Such a process accordingly introduces several additional processing steps which represent not only added capital and product-handling costs but also in the case of acetone separation an undesirable additional hazard. The Rhone-Poulenc specifications acknowledge that it might have been possible to employ an carboxylic acid chloride, instead of the anhydride, but point to the slowness of reaction given in French patent specification 2 164 619 (equivalent to USP 3925016) and they allege difficulty of separating the product from the reaction mixture and difficulties of eliminating HCl from the system.

In an article by Pueschel (Tenside, 7(5) p 249–54) in 1970 in a process similar to that of Rhone-Poulenc an acid acceptor, viz pyridine and DMF are present, the solvent is distilled off and the HCl is neutralised with sodium carbonate, so that separation of sodium chloride from the ester poses a problem. If a higher temperature is used to increase the reaction rate, Rhone-Poulenc suggest that coloured impurities would be formed, and thus they invite the conclusion that the skilled man in the art would set the carboxylic acid chloride route on one side. It is interesting to note that whilst they do not specify that the phenol sulphate salt must be anhydrous, their actions suggest strongly such a belief in that they submit it in their examples to a pre-reaction drying stage at 160° C at high vaccuum to 2600 pa, i.e. at about 1/40th atmospheric pressure. Clearly under such conditions substantially all water will have been removed.

The Procter & Gamble Company has described various methods for the manufacture of the esters. In EP-A-105672, they suggested that it is a conventional method to react the phenol sulphonate with an carboxylic acid halide in dioxan or dichloroethane, and indee a similar route using chlorobenzene is followed by Procter in EP-120591 Example 1. The specification highlights the tendency for such a system to foam, caused by sparging to help remove the gaseous hydrochloric acid, and warns that unless the HCl is removed efficiently there is likely to be formation of the less stable sulphonic acid form of the ester and sodium chloride. The formation of sodium chloride is stated as being disadvantageous, although the reason why is not given. Discouragingly, Procter also teaches that conversions in excess of 70% are difficult to obtain using an carboxylic acid halide. Instead, Procter advocates the use of a transesterification process in which a $C_2$–$C_3$ ester of phenol sulphonate is formed and then transesterified. The latter reaction is carried out using an excess of the higher molecular weight carboxylic acid as combined solvent/reactant. The specification alludes to potential problems of foaming during the trans-esterification and recognises that a further stage must in practice be introduced to separate residual carboxylic acid from ester product by dispersing the mixture in a solvent for the carboxylic acid which is a non-solvent for the ester, such as liquid aliphatic or aromatic hydrocarbons. It is also of interest to observe that the process specified the use of anhydrous phenol sulphonate. Thus, such a process is cumbersome, requiring distillation by removing part of the excess reagents and a solvation technique to remove the rest. Moreover, there is an inevitable residue of undesired low molecular weight ester Subsequently, Monsanto in EP-A-148148 sought to improve a process based upon carboxylic acid chlorides. They state explicitly that the prior processes using carboxylic acid chlorides suffered from the need for expensive solvents, long reaction times and expensive separation/clean-up procedures. Moreover, if small amounts of solvent were used gelled reaction products would be obtained which are hard to separate and recover as a solid product. Instead, Monsanto advocates a solvent-free process employing excess carboxylic acid chloride. Throughout, they stress that anhydrous conditions be maintained. Whilst such a process appears at first glance to offer the inherent advantage of greater space yield the fluid is more viscous, having a greater tendency to entrain the evolved HCl and this also renders solid/liquid separation considerably more difficult, slower and expensive. There is also a corresponding tendency for the product to smell unpleasantly. More recently, in EP-A221 045, Monsanto has further highlighted the requirement perceived by industry currently to employ anhydrous phenol sulphonate as reactant and has provided a method by which that need can be met involving high drying temperatures combined with sparging with an inert gas under non-oxidising conditions.

Additionally, we have found that the dehydration of sodium phenol sulphonate by azeotropy on a bulk scale poses tremendous difficulties in that the product tends to agglomerate and fuse together to form large lumps. These lumps interfere with the subsequent esterification, impairing not only the quality of the product but also the yield.

In EP-A-125641, Ethyl Corporation seeks to use a transesterification reaction between the phenol sulphonate and an alkyl aryl ester. They assert that it is preferred that the process be carried out under substantially anhydrous conditions, and that any water present in the reagents can be removed therefrom before the reaction by conventional techniques such as by azeotropic distillation with an organic solvent such as hexane, octane, toluene, xylenes and the like. Strictly speaking, the technique comprises co-removal by entrainment of water in the solvent rather than the classical formation of an azeotrope. Ethyl Corp. in their Examples indeed demonstrate azeotropic solvent/water removal, but only on a small laboratory scale, dewatering less than 0.1 moles of sodium phenol sulphonate in each batch.

In EP-A-164786, Shell International Research address the problem of making a branched carboxylic acid ester of the phenol sulphonate and advocate the substitution of the potassium salt for the sodium salt in order to obtain products having a higher purity than the 84% obtained with the sodium salt. It is noteworthy that the main difference between the two salts is that the sodium salt is normally obtained in the form of a dihydrate and for use in esterifications has been dehydrated whereas the potassium salt is normally produced in anhydrous form so that the likelihood of residual water interfering with the reaction is much reduced. Shell insist that the sodium salt is dewatered before use, both in the text and in their comparative Example, and offer drying or azeotropic distillation as a suitable method. They employ an 18 hour drying stage at 150° C. under reduced pressure, 20 kPa, i.e. about 1/5th atmospheric pressure. The scale of the Examples was only 0.2 moles phenol sulphonate.

Summarising the disclosures in the prior specifications, it can be seen that many large and successful companies in the chemical field have investigated processes for the preparation of esters of oxybenzene sulphonate salts, and three conclusions of note can be made. First, there is a broad concensus that such esters can be made with some degree of success by reaction between a carboxylic acid chloride and a phenol sulphonate salt, but particularly for laboratory scale preparationsand that there are problems associated with such a route which lead some researchers to advocate an alternative route and lead the remaining researchers to suggesting solutions to those problems. The second conclusion is that the presence of water in the reaction is deleterious, even the relatively small amount which is imported as the hydrate of the phenol sulphonate salt. The third conclusion, which is implicit in their choice of reaction medium, is that it should comprise an organic solvent or mixture, possibly employing an excess of liquid carboxylic acid chloride reactant therefor. The literature includes an alternative technique in which some carboxylic acid chlorides can react with some alcohols to form esters, characterised by the use of an aqueous alkaline reaction medium, sometimes called the Schotten-Baumann technique when aromatic carboxylic acid chlorides are used. The technique is normally considered only when two pre-requisite conditions are both met, namely that the selected carboxylic acid chloride is resistant to hydrolysis and the resultant ester is not only resistant to hydrolysis but is also substantially insoluble in the reaction medium.

Hitherto, there appears to be no published reference to any attempt to apply the Schotten-Baumann technique to the preparation of esters of oxybenzene sulphonate salts. This may be attributable in part to the emphasis that current researchers in the field have recently given to the problems associated with the presence of water of hydration in the phenol sulphonate starting material. Additionally, it is highly probable that the researchers may also have taken into account the fact that the esters of oxybenzene sulphonate salts are amongst the most soluble types of solid compounds that have received long-term acceptability as peroxyacid generators, sometimes otherwise referred to as bleach activators, and the fact that many acid chlorides that might be contemplated for use in Schotten-Baumann reactions can favour the competetive reaction, namely hydrolisis, in alkaline conditions. Indeed, there is some reasonable justification for the reticence of researchers to use this technique in that, for example, attempts to make nonanoyl oxybenzene carboxylate salt from a phenol carboxylate, a close relative of phenol sulphonate, resulted in an unsatisfactorily poor yield of the desired product.

W.J. Hickinbottom in his book Reactions of Organic Compounds on page 98 describes the use of the Schotten-Baumann method for making phenyl benzoate. When the method was repeated, but substituting sodium phenol sulphonate for phenol on an equimolar basis and using an excess of benzoyl chloride instead of excess phenol sulphonate salt, the result was also somewhat discouraging in that the yield of product recovered was less than 30% of the theoretical amount, based on the phenol sulphonate. Markedly higher efficiencies can be obtained using the organic solvent-based techniques so that this result would seem accordingly to substantiate the reluctance of the art to apply the aqueous technique for the preparation of the instant esters.

It is an object of the present invention to identify process conditions in which benzoyl oxybenzene sulphonate salts can be obtained in improved yields in an aqueous process.

According to the present invention there is provided a process for the production of benzoyl oxybenzene sulphonate salts in which an alkali metal phenol sulphonate is mixed with at least an equimolar amount of benzoyl chloride in the presence of a restricted amount of water and base. The invention is applicable to any alkali metal phenol sulphonate as starting material, and the variations can include the sulphonate substituent being in the 2, 3 or 4 position on the benzene nucleus and any alkali metal being present. The invention is particularly advantageous when employing the sodium salt of 4-sulphophenol and any others that share with it the feature of being hydrated in the normally available material. The prior art has taught the great desirability of first dehydrating the material, a non-trivial operation, whereas for the present invention process no such pre-dehydration step is needed, and similar results are obtained whether or not pre-hydration is employed. Of course, anhydrous phenol sulphonate salts can readily be used if they are available, including particularly potassium phenol sulphonate.

It is an important feature of the present invention that the amount of both water and base be constrained quite closely, in view of the findings of the inventors that it is by so doing that yields can be improved. Thus, by the term restricted amount when applied to the water content of the reaction mixture is meant that the weight ratio of the total weight of water to phenol sulphonate salt excluding any water content is not greater than about 4.5:1 and preferably is not greater than 3.75:1. The water:salt weight ratio is advantageously is selected in the range of at least about 1.5:1 to allow the mixture to be stirred by conventional equipment throughout the reaction, ie not exceed a solids density of about 40%. In practice, the water:sulphonate salt ratio is often selected within the range of from 2.5:1 to 3.5:1. By so selecting that ratio, it is possible to obtain improved yield whilst introducing the sulphonate salt as a solution rather than partly as a suspension. In many convenient embodiments, the phenol sulphonate/water mixture is introduced into the reaction vessel as a substantially saturated solution of the former in the latter. The total water content will include any water contributed from the base and from the reagents, e.g. as water of hydration, as well as any added as such.

In the context of the base, the term restricted amount means that the mole ratio of base to phenol sulphonate salt is less than 2:1 and the ratio of base to benzoyl chloride is at least 1:1. It will be understood that if too much base is present during the reaction phase, the yield of product is reduced. It is particularly preferable to use an amount of base in the range of from 1.3 to 1.6 moles per mole of phenol sulphonate salt, and in some instances an especially preferred range is from 1.4:1 to 1.5:1. The base reacts with the hydrochloric acid released when the benzoyl chloride reacts with the phenol sulphonate salt, forming either an organic adduct or a metal chloride salt, depending on the nature of the base. Advantageously, such adducts or metal salts tend to be markedly more soluble than the oxybenzene sulphonate ester and thus can readily be separated therefrom because it remains in solution to a proportionately greater extent on precipitation of the sulphonate ester and/or because it can subsequently be removed preferentially by water washing. Thus, the disadvantage of sodium chloride co-production mentioned in the prior art organic processes ceases to be a disadvantage in the instant process.

The base can conveniently be selected from inorganic or organic bases, including especially alkali metal bases, of which sodium and potassium bases are both widely available. It will be recognised that when inorganic bases are employed, it is often desirable to match the metal in the base to that in the phenol sulphonate salt so as to avoid a mixed metal ester salt being obtained. Thus, for example, the use of sodium base and sodium phenol sulphonate will produce a solely sodium salt of the ester product. Of course, should such a mixture be wanted, then use of mismatched base and sulphonate salt can achieve this. It will be also recognised that the use of a potassium base with sodium phenol sulphonate has resulted in even better yields, on occasions, than has the use of the sodium/sodium reactant/reagent combination. In order to avoid the introduction of extraneous anions, it is often convenient to use hydroxides, or oxides as the base, or alternatively, bases such as carbonate or bicarbonate which amount to (hydr)oxides on release of a gas like carbon dioxide. The most often used base is sodium hydroxide.

It has been observed that as the ratio of base to phenol sulphonate salt falls, there is an increasing propensity for the isolated product to contain benzoic acid, as unwanted impurity therein. In a second aspect of the present invention, the inventors have found a means to reduce the extent of that problem, which comprises effecting the reaction in the presence of an effective amount of a surfactant and especially a non-ionic surfactant, specifically an ethoxylate surfactant. In the trials conducted to date to determine how much constitutes an effective amount improvements were observed when adding even only a very small proportion of the selected surfactant, such as less than 0.3% and at least 0.03%, %s being by weight of the reaction mixture. Some improvement is also obtained at even lower additions such as down to 0.005%. A much preferred range of surfactant concentration is from 0.03 to 0.1% since in that range the benefit of reduced benzoic acid residue occurs simultaneously with production of a readily filterable product. It will be understood that this additive can be employed under all the reaction conditions contemplated for the reaction, although it is much preferred to employ a base that does not generate carbon dioxide in situ when also using the surfactant.

The reaction preferably employs excess benzoyl chloride, advantageously at least a 10% molar excess over the phenol sulphonate salt, and beneficially at least a 20% molar excess. However, it will be recognised that in the corresponding prior art processes hitherto published it would often be necessary to use significantly higher excesses of the carboxylic acid chloride to obtain good product yield, so that the fact that excellent yields are obtainable with benzoyl chloride is molar excesses of only 20 to 30% represents a further advantage of the instant invention process compared with the prior art. Molar excesses of more than 30% of benzoyl chloride can be added if desired, such as selecting in the range of up to 100% molar excess, only at the expense of additional reactant cost.

The reaction forming the ester is mildly exothermic, and without control could heat the reaction mixture from ambient to over 50° C. under at least some reaction conditions and if no control was exercised. We prefer to cool the reaction mixture so as to maintain a temperature not in excess of 30° C., but of course a reaction temperature above 30° C. is feasible provided that the resultant increased benzoic acid impurity level can be tolerated. In particular, we wish to maintain the aqueous mixture in liquid form, but often below 20° C. In practice this will often mean a reaction temperature of at least 5° C. as a result of constraints imposed by cooling costs/apparatus, otherwise a temperature down to 0° C. is tolerable.

The preferred method of operation is to add the benzoyl chloride to the aqueous alkaline solution of phenol sulphonate salt, particularly in a progressive fashion, by which we mean that the benzoyl chloride is added during a substantial proportion of the total reaction period and is added either continuously or in small increments. By so doing, control of the reaction exotherm is rendered easier. The period of addition of the benzoyl chloride is normally at least 30 minutes and in many instances will be chosen within the period of 1 to 5 hours, although even longer periods of introduction can be employed, if desired. The period allowed for reaction after all the reactants have been added is often at least 30 minutes up to 4 hours, but its value in increasing the yield of product tends to become rather greater as the benzoyl chloride introduction period is shorter. The total reaction period, which is obtained by aggregating the period of addition of the second reactant to the first reactant, and the period allowed for reaction after all the reactants have been added, is normally at least 1 hour and often from 2 to 5 hours.

The reaction can conveniently be carried out in a well stirred reaction vessel equipped with a cooling jacket or other means for cooling the mixture, such as pumping through a cooling heat exchanger.

The crude solid product can be separated from the spent mother liquor by conventional apparatus and methods for separating particulate solids from liquids, and these include various types of filter and centrifuges. If desired, the mixture can be further cooled before the solids are removed. In many instances, the mixture will have a temperature in the range of about 5° C. to about 12° C. at the time of solids removal.

The purity of the crude reaction product depends upon the process of manufacture conditions employed, as has already been mentioned herein. Two of the main likely contaminants are respectively benzoic acid, by virtue of hydrolysis of either the benzoyl chloride or the ester, and the benzoate salt of the added base, e.g. sodium benzoate. Analysis of the product and experience will indicate the relative proportions of each. The latter can be readily removed from the crude product by water washing, by virtue of the greater rate of solubility of the benzoate salt compared with the phenol sulphonate salt. The level of benzoic acid can be reduced by washing with a dilute alkali solution such as caustic solution, which has the effect of neutralising benzoic acid and thereby solubilising it, preferably employing an equimolar amount of alkali to neutralise the acid or a small excess. It is, in practice, more convenient to carry out the neutralisation of the unwanted benzoic acid at the end of the ester manufacture reaction before the solids are separated from the spent mother liquor. The amount of alkali to add then can be readily determined by consideration of how much acid was generated in previous runs under the same reaction conditions.

It will be recognised that by suitably modifying and appropriately controlling the reaction conditions, the instant invention enables an aqueous route to be employed with all the consequential benefits gained by not having to use organic solvents in substantial amounts, such benefits including not only the avoidance of the hazards of such solvents but also the financial benefit of being able to employ the cheapest reaction medium. Advantageously, the invention process minimises the extent to which the product contains the phenol sulphonate starting material as impurity, whereas this was often a major problem in many of the prior art organic solvent-based processes. In addition, it will be seen that at least under the optimum conditions for the invention process, it is possible to achieve good yields not only when the basis is the phenol sulphonate reactant but also when the basis is the benzoyl chloride, since under those selected conditions the good yield is obtained with only a relatively small excess of the latter reactant.

It will further be recognised that the invention has been described with particular reference to batch mode of operation, but that it can be carried out felicitously as a continuous or semi-continuous process at the user's discretion, employing essentially the same process conditions. In such a continuous process, which can advantageously employ conventional reactive crystalliser equipment, the components of the reaction mixture are flowed into the reaction vessel continuously in the relative amounts within the ranges described hereinbefore for the batch process and at such rates in relation to the rate of withdrawing reaction mixture from the vessel as to obtain a residence time in the vessel that is preferably selected in the range of from 30 minutes to 5 hours, and particularly about 1 to 3 hours. Although it may be convenient to flow three separate reagent streams into the vessel, namely benzoyl chloride, an aqueous suspension or preferably aqueous solution of the phenol sulphonate and an aqueous solution of the base, the two latter streams can be combined, if desired. Accordingly, in a pre-mixing step, which can be carried out at elevated temperature if desired, the phenol sulphonate is predissolved to form the aqueous solution, preferably at or near saturation, optionally also containing the restricted amount of base. By way of illustration only, one eminently suitable set of embodiments employs a benzoyl chloride stream and an aqueous alkali/phenol sulphonate stream inflowed at respectively 4 and 19 parts w/w per minute into a vessel containing substantially constantly or on average about 2000 parts w/w reaction mixture, the aqueous component consisting of about 7.1% w/w sodium hydroxide, about 28.6% w/w sodium phenol sulphonate and about 64.3% water and optionally also a trace of surfactant. The reaction mixture is preferably maintained to within a temperature band of 5 to 12° C., by appropriate cooling.

It is particularly convenient to withdraw reaction mixture continuously from the vessel, and at a rate that matches the rate of inflow of reactants, thereby maintaining in essence a constant volume and steady state conditions in the vessel, although periodic withdrawal is an alternative option. The withdrawn reaction mixture, which is a slurry of solid ester product suspended in an aqueous medium is then fed to a conventional solid/liquor separator, preferably operated continuously, possibly via a stirred holding tank in which residual benzoic acid can be neutralised with added base.

Having described the invention in general terms, specific embodiments will now be given some detail by way of example only. For the avoidance of doubt, the invention is not limited to these specific embodiments.

In the following embodiments of the invention process and comparisons the procedure adopted was that an aqueous alkaline solution was made up by dissolving the amount of base specified in the Table in the amount of demineralised water, which was then cooled to about 20° C. The specified amount of sodium phenol sulphonate dihydrate (designated SPS) and any surfactant in the specified amount were introduced and the mixture stirred until it became clear, indicating that the starting material had entered into solution. The other reactant, benzoyl chloride (designated BzCl) was then introduced progressively during the addition period specified as Addn Time with agitation and permitted to react also during the further period (React Time) also specified, the temperature being controlled within the limits given. At the end of the reaction period, the mixture either was at, or was cooled to about 0 to 5° C. and filtered. The filter cake was then washed with ice water and dried at about 50° C.

The theoretical yield is based on phenol sulphonate salt. It will be noted that in runs ref A to S, the base used was sodium hydroxide and in runs ref T to X, the base was potassium hydroxide. In all runs except T, U and V, the surfactant when used was an alcohol ethoxylate available under the trademark "EMPILAN KM50" and in T, U and V it was an anionic surfactant available under the trademark NANSA SS60. The results are summarised in the Table.

THE TABLE

| Run Ref. | A | B | C | D | E | F |
|---|---|---|---|---|---|---|
| Water (g) | 72.65 | 46 | 40 | 46 | 40 | 40 |
| NaOH (g) | 7.5 | 4.6 | 4.6 | 3.98 | 4.6 | 3.98 |
| SPS (g) | 17.35 | 17.75 | 17.75 | 17.75 | 17.75 | 17.75 |
| BzCl (g) | 12.46 | 12.95 | 11.37 | 12.95 | 12.9 | 12.95 |

THE TABLE-continued

| Surfactant Mole Ratio of | | | | | | |
|---|---|---|---|---|---|---|
| NaOH:SPS | 2.5 | 1.5 | 1.5 | 1.3 | 1.5 | 1.3 |
| BzCl:SPS | 1.18 | 1.2 | 1.06 | 1.2 | 1.2 | 1.2 |
| Addn Time mins | 15 | 29 | 43 | 29 | 27 | 19 |
| React Time mins | 61 | 52 | 63 | 61 | 52 | 54 |
| React.Temp °C. | 25 | 23 | 20 | 22 | 21 | 22 |
| Filter Temp °C. | 2 | 2 | 2 | 0 | 0 | 1 |
| Water Wash (g) | 0 | 20 | 20 | 20 | 2 | 20 |
| Product Yield (g) | 5.81 | 21.88 | 17.46 | 20.57 | 18.5 | 22.61 |
| % theoretical | 25.9 | 95.3 | 76.0 | 89.6 | 80.6 | 98.5 |
| % Benzoic Acid | 0 | 6.9 | 4.6 | 8.1 | 5.1 | 8.05 |

| Run Ref. | G | H | I | J | K | L |
|---|---|---|---|---|---|---|
| Water (g) | 40 | 48 | 43 | 46 | 46 | 120 |
| NaOH (g) | 3.98 | 7.65 | 6.12 | 5.2 | 5.2 | 13.3 |
| SPS (g) | 17.75 | 17.75 | 17.75 | 17.75 | 17.75 | 53.25 |
| BzCl (g) | 11.83 | 11.85 | 11.85 | 12.91 | 12.91 | 38.73 |
| Surfactant (g) | | | | 0.17 | 0.17 | 0.5 |
| Mole Ratio | | | | | | |
| NaOH:SPS | 1.3 | 2.5 | 2.0 | 1.7 | 1.7 | 1.45 |
| BzCl:SPS | 1.1 | 1.1 | 1.1 | 1.2 | 1.2 | 1.2 |
| Addn Time mins | 37 | 39 | 33 | 33 | 35 | 90 |
| React Time mins | 76 | 60 | 68 | 90 | 135 | 150 |
| React.Temp °C. | 24 | 22 | 22 | 22 | 23 | 5 |
| Filter Temp °C. | 1 | 0 | 0 | 2 | 23 | 10 |
| Water Wash (g) | 10 | 10 | 10 | 11.5 | 11.5 | 30 |
| Product Yield (g) | 20.79 | 10.35 | 14.35 | 19.4 | 17.61 | 69.8 |
| % theoretical | 90.6 | 45 | 62.5 | 84.6 | 76.7 | 101.5 |
| % Benzoic Acid | 8.1 | 0 | 4.81 | 0.5 | 6.5 | <0.1 |

| Run Ref. | M | N | O | P | Q | R | S |
|---|---|---|---|---|---|---|---|
| Water (g) | 120 | 120 | 120 | 120 | 120 | 120 | 120 |
| NaOH (g) | 13.3 | 13.3 | 13.3 | 13.3 | 13.3 | 13.3 | 13.3 |
| SPS (g) | 53.25 | 53.25 | 53.25 | 53.25 | 53.25 | 53.25 | 53.25 |
| BzCl (g) | 38.73 | 38.73 | 38.73 | 38.73 | 37.2 | 12.91 × 3 | 38.73 |
| Surfactant (g) | 0.5 | 0.5 | — | 0.5 | 0.5 | 0.5 | 0.1 |
| Mole Ratio | | | | | | | |
| NaOH:SPS | 1.45 | 1.45 | 1.45 | 1.45 | 1.45 | 1.45 | 1.45 |
| BzCl:SPS | 1.2 | 1.2 | 1.2 | 1.2 | 1.15 | 1.2 | 1.2 |
| Addn Time mins | 90 | 90 | 90 | 90 | 90 | 90 | 90 |
| React Time mins | 120 | 120 | 120 | 120 | 90 | 60 | 60 |
| React.Temp °C. | 5–20 | 5–20 | 5 | 5 | 5–20 | 5 | 5 |
| Water Wash (g) | 30 | 50 | 50 | 50 | 50 | 50 | 50 |
| Product Yield (g) | 67.21 | 61.35 | 67.85 | 69.62 | 59.64 | 72.97 | 74.18 |
| % theoretical | 97.7 | 89.0 | 98.5 | 101.1 | 86.6 | 106.0 | 107.7 |
| % Benzoic Acid | <0.1 | 1.0 | 0.5 | 0 | 0 | <0.1 | 0 |

| Run Ref. | T | U | V | W | X |
|---|---|---|---|---|---|
| Water (g) | 120 | 120 | 120 | 120 | 120 |
| KOH (g) | 21.84 | 21.84 | 21.84 | 19.5 | 19.5 |
| SPS (g) | 53.25 | 53.25 | 53.25 | 53.25 | 53.25 |
| BzCl (g) | 38.73 | 35.3 | 38.73 | 38.73 | 38.73 |
| Surfactant (g) | 0.5 | 0.5 | 0.5 | 0.5 | 0.5 |
| Mole Ratio | | | | | |
| KOH:SPS | 1.45 | 1.45 | 1.45 | 1.3 | 1.3 |
| BzCl:SPS | 1.2 | 1.1 | 1.2 | 1.2 | 1.15 |
| Addn Time mins | 90 | 60 | 90 | 90 | 90 |
| React Time mins | 180 | 120 | 120 | 120 | 120 |
| React.Temp °C. | 5 | 20–5 | 30–20 | 15–5 | 15–5 |
| Water Wash (g) | 20 | 30 | 30 | 30 | 30 |
| Product Yield (g) | 67.21 | 61.35 | 68.61 | 86.29 | 90.17 |
| % Theoretical | 97.6 | 89.1 | 99.6 | 125.3 | 130.9 |
| % Benzoic Acid | 3.1 | <0.1 | 1.5 | <0.1 | <0.1 |

From the Table, it can be seen that in the first run, viz A, a yield of only 27% was obtained, based on the phenol sulphonate starting material. This poor yield was attributable in particular to the high mole ratio of alkali to phenol sulphonate and to the low ratio of reactants to reaction medium employed. By comparison with subsequent trials B, H and I, it can be seen that the best results are clearly obtained when the mole ratio of base to hydrated phenol sulphonate was reduced to 1.5:1 or lower and also when the amount of added water was at its lowest. The effect of varying the ratio of benzoyl chloride to phenol sulphonate can be seen by comparing trials C and E, and also F and G. Two points stand out. First, a surprisingly high yield of product was obtained even at molar excess of benzoyl chloride of only 6% or 10%, and secondly even better yields were gained when the excess was increased slightly to 20%.

From trials A to I, it can be seen that broadly as the yield increased, there was an increased tendency of the product to contain benzoic acid, and that by incorporating the surfactant, its content was markedly reduced, particularly by comparing J and L. The effect of temperature during the reaction can be seen by noting that the yield in trials M and O and P were somewhat better than that in N, and also that the benzoic acid residue in N was worse.

From trials T to X it can be seen that it is possible to use another base and also that the alcohol ethoxylate surfactant was more successful at controlling benzoic acid residue than was an alkyl benzene sulphonate surfactant. It is also noticeable that with this base, even better yields were obtained.

We claim:

1. In a process for the production of benzoyl oxybenzene sulphonate salts in which an alkali metal phenol sulphonate is mixed with benzoyl chloride and permitted to remain in contact until at least some benzoyl oxybenzene sulphonate has formed the improvement which comprises essentially employing at least an equimolar amount of benzoyl chloride in the presence of a restricted amount of water and base.

2. A process according to claim 1 in which the phenol sulphonate is a 4-sulphophenol salt.

3. A process according to claim 1 in which the sulphophenol salt is the sodium salt.

4. A process according to claim 1 in which the sulphophenol salt is hydrated.

5. A process according to claim 1 in which the phenol sulphonate is hydrated 4-sulphophenol, sodium salt.

6. A process according to claim 1 in which the weight ratio of the total weight of water to phenol sulphonate salt excluding any water content of said sulphonate salt is not greater than about 4.5:1.

7. A process according to claim 6 in which the weight ratio of the total weight of water to phenol sulphonate salt excluding any water content of said sulphonate salt is not greater than 3.75:1.

8. A process according to claim 7 in which the total water:phenol sulphonate weight ratio in the reaction mixture is within the range 2.5:1 to 3.5:1.

9. A process according to claim 1 in which the mole ratio of base to phenol sulphonate salt is less than 2:1.

10. A process according to claim 9 in which the mole ratio of base to phenol sulphonate salt is from 1.3:1 to 1.6:1.

11. A process according to claim 10 in which the mole ratio of base to phenol sulphonate salt is from 1.4:1 to 1.5:1.

12. A process according to claim 1 in which benzoyl chloride is employed in an excess of at least 10% molar over the amount of phenol sulphonate.

13. A process according to claim 12 in which benzoyl chloride is employed in an excess of up to 30% molar over the amount of phenol sulphonate.

14. A process according to claim 1 in which the total water:phenol sulphonate weight ratio in the reaction mixture is within the range 1.5:1 to 3.75:1, the mole ratio of base to phenol sulphonate salt is from 1.3:1 to 2:1, the amount of benzoyl chloride employed is an excess of at least 10% molar up to 30% molar over the amount of phenol sulphonate employed.

15. A process according to claim 1 in which the total water:phenol sulphonate weight ratio in the reaction mixture is within the range 2.5:1 to 3.5:1, the mole ratio of base to phenol sulphonate salt is from 1.4:1 to 1.5:1.

16. A process according to claim 1 or 14 in which the reaction is carried out at a temperature of from 0 to 30° C.

17. A process according to claim 16 in which the reaction is carried out at a temperature of from 5 to 20° C.

18. A process according to claim 15 in which the reaction is carried out at a temperature of from 5 to 12° C.

19. A process according to claim 1 or 14 in which the reaction is carried out in the presence of an effective amount of a surfactant.

20. A process according to claim 19 in which the surfactant is an alcohol ethoxylate.

21. A process according to claim 19 in which the base employed does not generate carbon dioxide.

22. A process according to claim 19 in which the effective amount is selected in the range of not more than 0.5% by weight of the reaction mixture.

23. A process according to claim 22 in which the effective amount is selected in the range of from 0.03 to 0.1% by weight of the reaction mixture.

24. A process according to claim 1 or 14 which is carried out in batch mode and in which the benzoyl chloride is added progressively to an aqueous alkaline solution of the phenol sulphonate salt.

25. A process according to claim 24 in which the benzoyl chloride is added during a period of from 0.5 to 5 hours.

26. A process according to claim 24 in which the reaction period is from 1 to 5 hours.

27. A process according to claim 26 in which the reaction is carried out at a temperature in the range of from 5 to 20° C.

28. A process according to claim 1 or 14 in which the benzoyl chloride, base, phenol sulphonate and water are introduced continuously into an agitated body of reaction mixture from which a portion is withdrawn continuously or intermittently, the rates of introduction of the reagents and withdrawal of the portion of reaction mixture being so controlled that the residence time of the mixture is from 0.5 to 5 hours.

29. A process according to claim 28 in which the reagents are introduced into the body in two streams, one stream consisting essentially of benzoyl chloride and the second stream consisting essentially of the water, base and phenol sulphonate, and optionally a trace amount of surfactant.

30. A process according to claim 29 in which the reaction is carried out at a temperature in the range of from 5 to 20° C.

31. A process according to claim 1 or 14 in which residual benzoic acid in the reaction mixture at the end of the batch reaction or in the portion of mixture withdrawn from the body of reaction mixture is neutralised before the solid product is separated from the mother liquor.

32. A process according to claim 31 in which the separated solid product is water washed to remove impurities.

* * * * *